United States Patent
Martin et al.

(10) Patent No.: US 10,201,640 B2
(45) Date of Patent: Feb. 12, 2019

(54) ULTRAFINE ELECTROSPUN FIBERS OF POLY-4-HYDROXYBUTYRATE AND COPOLYMERS THEREOF

(71) Applicant: Tepha, Inc., Lexington, MA (US)

(72) Inventors: David P. Martin, Arlington, MA (US); Kai Guo, Waltham, MA (US); Said Rizk, Windham, NH (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 670 days.

(21) Appl. No.: 13/800,871

(22) Filed: Mar. 13, 2013

(65) Prior Publication Data

US 2014/0277572 A1  Sep. 18, 2014

(51) Int. Cl.
*A61L 31/14* (2006.01)
*A61F 2/00* (2006.01)
(Continued)

(52) U.S. Cl.
CPC ............. *A61L 31/14* (2013.01); *A61F 2/00* (2013.01); *A61F 2/28* (2013.01); *A61L 15/26* (2013.01);
(Continued)

(58) Field of Classification Search
CPC ....... D01D 5/0038; D01F 6/625; C08L 67/04; A61L 17/105; A61L 31/14; A61L 31/146; A61F 2/28; D04H 1/728
(Continued)

(56) References Cited

U.S. PATENT DOCUMENTS 5,811,272 A    9/1998 Snell
6,245,537 B1   6/2001 Williams
(Continued)

FOREIGN PATENT DOCUMENTS

CN    101144196    * 3/2008 ............... D01D 5/24
EP    2505213      10/2012
(Continued)

OTHER PUBLICATIONS

Ellison, Christopher "Melt Blown nanofibers: Fiber diameter distributions and onset of fiber breakup", www.sciencedirect; Apr. 10, 2007.*
(Continued)

*Primary Examiner* — Jennifer A Steele
(74) *Attorney, Agent, or Firm* — Pabst Patent Group LLP (57) ABSTRACT

Methods to produce structures containing ultrafine fibers with average diameters from 10 nm to 10 μm and more preferably from 50 nm to 5 μm, have been developed. These methods produce ultrafine fibers without substantial loss of the polymer's weight average molecular weight. The ultrafine electrospun fibers have an unexpectedly higher degree of molecular orientation, and higher melt temperature than fibers derived by dry spinning. In the preferred embodiment, the polymer comprises 4-hydroxybutyrate. The ultrafine fibers are preferably derived by electrospinning. A solution of the polymer is dissolved in a solvent, pumped through a spinneret, subjected to an electric field, and ultrafine fibers with a high degree of molecular orientation are collected. These structures of ultrafine fibers can be used for a variety of purposes including fabrication of medical devices.

26 Claims, 3 Drawing Sheets

(51) Int. Cl.

| | | |
|---|---|---|
| *A61L 17/14* | (2006.01) | |
| *A61L 17/10* | (2006.01) | |
| *A61L 15/42* | (2006.01) | |
| *A61L 27/34* | (2006.01) | |
| *A61L 31/10* | (2006.01) | |
| *A61L 27/56* | (2006.01) | |
| *A61L 15/26* | (2006.01) | |
| *D01F 6/62* | (2006.01) | |
| *C08L 67/04* | (2006.01) | |
| *D01D 5/00* | (2006.01) | |
| *A61L 27/18* | (2006.01) | |
| *A61L 2/28* | (2006.01) | |
| *A61F 2/28* | (2006.01) | |

(52) U.S. Cl.
CPC ............ *A61L 15/425* (2013.01); *A61L 17/105* (2013.01); *A61L 17/145* (2013.01); *A61L 27/34* (2013.01); *A61L 27/56* (2013.01); *A61L 31/10* (2013.01); *A61L 31/146* (2013.01); *D01D 5/0038* (2013.01); *D01F 6/625* (2013.01); *A61L 2400/12* (2013.01); *Y10T 428/249953* (2015.04); *Y10T 428/298* (2015.01); *Y10T 442/10* (2015.04); *Y10T 442/681* (2015.04)

(58) Field of Classification Search
USPC .......................................... 442/334, 340, 351
See application file for complete search history.

(56) References Cited

U.S. PATENT DOCUMENTS

| | | | |
|---|---|---|---|
| 6,316,262 B1 | 11/2001 | Huisman | |
| 6,323,010 B1 | 11/2001 | Skraly | |
| 6,548,569 B1 | 4/2003 | Williams | |
| 6,623,748 B2 | 9/2003 | Clokie | |
| 6,838,493 B2 | 1/2005 | Williams | |
| 6,867,247 B2 | 3/2005 | Williams | |
| 6,905,987 B2 | 6/2005 | Noda | |
| 7,179,883 B2 | 2/2007 | Williams | |
| 7,244,442 B2 | 7/2007 | Williams | |
| 7,268,205 B2 | 9/2007 | Williams | |
| 7,553,923 B2 | 6/2009 | Williams | |
| 7,618,448 B2 | 11/2009 | Schmitz | |
| 7,641,825 B2 | 1/2010 | Rizk | |
| 8,016,883 B2 | 9/2011 | Coleman | |
| 8,034,270 B2 | 10/2011 | Martin | |
| 8,039,237 B2 | 10/2011 | Martin | |
| 8,231,889 B2 | 7/2012 | Williams | |
| 8,287,909 B2 | 10/2012 | Martin | |
| 2005/0158542 A1* | 7/2005 | Iwata et al. .................. | 428/364 |
| 2009/0012604 A1* | 1/2009 | Schmitz et al. ............. | 623/1.42 |
| 2009/0162276 A1* | 6/2009 | Martin et al. ................ | 424/1.11 |
| 2011/0236974 A1* | 9/2011 | Ogle et al. ................... | 435/375 |
| 2013/0218253 A1* | 8/2013 | Kaufmann .............. A61L 27/56 623/1.2 |

FOREIGN PATENT DOCUMENTS

| | | | |
|---|---|---|---|
| WO | 2009085823 | 7/2009 | |
| WO | 2011106205 | 9/2011 | |
| WO | 2011119742 | 9/2011 | |
| WO | 2011159784 | 12/2011 | |
| WO | WO 2011159784 A1 * | 12/2011 | ............ A61L 27/18 |
| WO | 2012064526 | 5/2012 | |

OTHER PUBLICATIONS

Martin, et al., "Medical Applications of Poly-4-hydroxybutyrate: A Strong Flexible Absorbable Biomaterial", Biochem. Eng. J.16:97-105 (2003).

\* cited by examiner

ULTRAFINE ELECTROSPUN FIBERS OF POLY-4-HYDROXYBUTYRATE AND COPOLYMERS THEREOF

FIELD OF THE INVENTION

The present invention generally relates to structures containing ultrafine fibers that have been formed by electrospinning of poly-4-hydroxybutyrate (P4HB) and copolymers thereof. The ultrafine fibers produced by electrospinning have average diameters in the nanometer range whereas fibers produced by melt extrusion and dry spinning have diameters in the micron range. The ultrafine fibers have higher melt points than fibers derived from dry spinning. The structures containing ultrafine fibers include medical devices that can be used in tissue engineering, tissue regeneration, tissue separation, tissue repair, tissue replacement, and drug delivery. These medical devices have high surface area to volume ratios that help to promote cell attachment and tissue in-growth.

BACKGROUND OF THE INVENTION

Poly-4-hydroxybutyrate (P4HB) and copolymers thereof can be produced using transgenic fermentation methods, see, for example, U.S. Pat. No. 6,548,569 to Williams et al., and are produced commercially, for example, 20 by Tepha, Inc. (Lexington, Mass.). Poly-4-hydroxybutyrate (P4HB, TephaFLEX® biomaterial) is a strong, pliable thermoplastic polyester that, despite its biosynthetic route, has a relatively simple structure. Upon implantation, P4HB hydrolyzes to its monomer, and the monomer is metabolized via the Krebs cycle to carbon dioxide and water.

The polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, and relative ease of production using recombinant bacteria or plants. Chemical synthesis of P4HB has been attempted, but it has been impossible to produce the polymer with a sufficiently high molecular weight that is necessary for most applications (see Hori, Y., et al., *Polymer* 36:4703-4705 (1995) and Houk, K. N., et al., *J. Org. Chem.,* 2008, 73 (7), 2674-2678).

U.S. Pat. Nos. 6,245,537, 6,623,748, 7,244,442, and 8,231,889 describe methods of making PHAs with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), and by Martin, D. et al. Medical Applications of Poly-4-20 hydroxybutyrate: A Strong Flexible Absorbable Biomaterial, *Biochem. Eng. J.* 16:97-105 (2003). Medical devices and applications of P4HB have also been disclosed by WO 00/56376 to Williams et al. Several patents including U.S. Pat. Nos. 6,555,123, 6,585,994, and 7,025,980 describe the use of PHAs in tissue repair and engineering.

U.S. Pat. No. 8,034,270 to Martin et al. discloses monofilament and multifilament knitted meshes of P4HB produced by knitting monofilament and multifilament fibers of P4HB. WO 2011/119742 to Martin et al. discloses P4HB monofilament and multifilament fiber, coatings and spin finishes for these fibers, and medical devices made from P4HB monofilament and multifilament fibers. U.S. Pat. No. 8,016,883 to Coleman et al. discloses methods and devices for rotator cuff repair, including medical devices containing knitted meshes of P4HB and non-wovens made from P4HB multifilament fibers.

U.S. Pat. No. 8,287,909 to Martin et al. discloses medical devices containing melt-blown non-wovens of poly-4-hydroxybutyrate and copolymers thereof with average fiber diameters of 1 μm to 50 μm. Notably, the process of melt blowing results in a significant drop in the molecular weight of P4HB which can be a disadvantage if it is desirable to retain mechanical properties, such as burst strength, in vivo, for a prolonged period of time.

WO 2011/159784 to Cahil et al. discloses medical devices containing dry spun non-wovens of P4HB and copolymers thereof, and continuous processing methods for their preparation. The fibers of the non-wovens have average diameters in the micron range.

A low melting and high modulus electrospun scaffold made from a blend of P4HB and poly(ε-caprolactone) (80:20), and spun from a 7.5 wt./v-% THF solution, is disclosed by Vaz, C. M. et al., Novel Electrospun P4HB: PCL Scaffold for Aortic Valve Tissue Engineering, Poster Presentation (2004), Eindhoven University of Technology. Notably, blending poly(ε-caprolactone) with P4HB significantly depresses the melting temperatures of both poly(ε-caprolactone) and P4HB. The blended scaffold has a melting point of 40° C., which is significantly lower than the melting point of 58-60° C. for P4HB, and as such has very limited commercial use due to its thermal instability at relatively low temperatures. Since both polymers are thermoplastics, significant physical changes occur upon implantation of this blend in the body, since the melting temperature of the blend is only 3° C. above body temperature, and the blend would likely melt in a patient with an elevated temperature.

WO 95/23249 to Noda et al. discloses fabrics prepared from other polyhydroxyalkanoates, namely, poly-3-hydroxybutyrate (PHB) and poly-3-hydroxybutyrate-co-3-hydroxyvalerate (PHBV) by dry spinning for use in non-medical applications such as disposable absorbent articles, including diapers, incontinence articles, and sanitary napkins. These materials, however, have substantially different thermal and physical properties than poly-4-hydroxybutyrate and copolymers thereof. For example, PHB has a melting point and glass transition temperature of approx. 180° C. and 1° C., respectively, and an elongation to break of about 3%, whereas P4HB has a melting point of 60° C., a glass transition temperature of approx. −51° C., and elongation to break of around 1,000%. As such, PHB is a brittle polymer that has properties resembling polystyrene whereas P4HB is a strong but extensible polymer similar to low density polypropylene. Furthermore, PHB and PHBV have also been reported to degrade very slowly in vivo with material still present after 24 months (Duvernoy, O. et al. A biodegradable patch used as a pericardial substitute after cardiac surgery: 6- and 24-month evaluation with CT, *Thorac. Cardiovacs. Surgeon,* 43:271-274 (1995)), and are therefore not well suited for many in vivo surgical applications.

In the practice of surgery there currently exists a need for structures containing ultrafine degradable fibers with improved performance. These structures can be used, for example, in both soft and hard tissue repair, to reinforce tissue structures, to separate tissues, to regenerate tissues, and to replace tissues. The ultrafine fibers can also be used as components of other device structures.

Ultrafine fibers may be made by electrospinning. This process produces unusually small diameter fibers with average diameters in the nanometer range typically from about 10 nm to 10 μm or more narrowly from about 50 nm to about 5 μm. In contrast, melt extrusion and dry spinning typically produce fibers with diameters in the micron range.

The equipment for electrospinning typically comprises a spinneret connected to a high voltage direct current, and a grounded collector plate. In the laboratory, a hypodermic syringe needle is frequently used as the spinneret, but a plurality of nozzles may also be used. To make ultrafine fibers, the polymer material to be electrospun is dissolved in a solvent, and pumped through the spinneret under a constant pressure or flow rate. As the polymer material solution emerges from the spinneret, the liquid surface of the solution is charged as it becomes subjected to the electric field. As the strength of the field increases and overcomes the surface tension, the hemispherical surface of the polymer material solution at the spinneret begins to elongate, and forms a conical shape known as the Taylor cone. At a critical point, when the electric field force overcomes the surface tension at the spinneret, a charged jet of the polymer material solution is ejected from the Taylor cone and travels toward the collector plate, provided the molecular cohesion of the solution is sufficiently strong. During transit, the solvent evaporates from the jet to form a charged ultrafine fiber that is deposited at the collector plate. If desired, compressed air or other gas may be injected adjacent to the spinneret to help form the desired nanofibers.

The properties of electrospun fibers may be tailored by varying certain parameters of the electrospinning process. These include (i) solvent and solution properties, such as viscosity, conductivity, evaporation rate, concentration and surface tension, (ii) equipment set up conditions, such as the distance between the spinneret and collector plate, the electric potential applied, and the pressure or flow rate of the polymer material solution, (iii) atmospheric conditions, such as temperature, humidity, and any applied air velocity between the spinneret and collector plate, and (iv) polymer properties such as Mw, composition, melting properties, thermal properties and crystallization rate. It is also possible to set up the electrospinning equipment such that the spinneret and/or the collector plate are moving relative to one another in order to produce different electrospun structures and shapes.

A number of absorbable materials have been used to produce ultrafine fibers for use in surgery. For example, ultrafine fibers have been made from polyglycolic acid (PGA) or copolymers containing lactic acid. These materials do not, however, have ideal properties for many procedures and applications. For example, ultrafine fibers made from glycolic acid containing polymers degrade quickly, are moisture sensitive and release acidic degradation products that can cause inflammatory reactions.

It is therefore an object of the invention to provide continuous processes for production of ultrafine fibers of P4HB and copolymers thereof, which can be incorporated into or formed into medical devices with excellent physical and mechanical properties for medical applications.

It is an object of the present invention to provide methods to produce electrospun ultrafine fibers of absorbable P4HB and copolymers thereof that have average diameters from 10 nm to 10 μm and more preferably from 50 nm to 5 μm, and high surface areas to volume ratios.

It is a further object of the present invention to provide methods to produce electrospun ultrafine fibers of absorbable P4HB and copolymers thereof without substantial loss of the polymer molecular weight during processing.

It is still a further object of the present invention to provide methods to produce electrospun ultrafine fibers of absorbable P4HB and copolymers thereof with a high degree of molecular orientation in the fibers.

It is yet another object of the present invention to provide methods to produce electrospun ultrafine fibers of absorbable P4HB wherein the polymer has a melting point which is higher than the melting point of P4HB fibers formed by dry spinning.

It is another object of the present invention to provide continuous processes to produce medical devices containing ultrafine fibers of P4HB and copolymers thereof by electrospinning, including processes to form medical devices by coating other materials and scaffolds with electrospun ultrafine fibers, and processes to electrospin P4HB and copolymers thereof into ultrafine fibers without substantial loss of molecular weight during the spinning process.

SUMMARY OF THE INVENTION

Methods to produce structures containing ultrafine fibers with average diameters from 10 nm to 10 μm, more preferably from 50 nm to 5 μm, have been developed. These methods allow the ultrafine fibers to be produced without substantial loss of the polymer weight average molecular weight. In the preferred embodiment, the polymer comprises 4-hydroxybutyrate. In one embodiment, the polymer is dissolved in a solvent, the polymer solution is pumped through a spinneret, subjected to an electric field, and ultrafine fibers with a high degree of molecular orientation are collected. These structures of ultrafine fibers can be used for a variety of purposes including fabrication of medical devices.

Also provided are structures containing/including ultrafine fibers of poly-4-hydroxybutyrate or copolymer thereof, wherein the structure of ultrafine fibers is derived by electrospinning. The ultrafine fibers have average diameters ranging from 10 nm to 10 μm, more preferably from 50 nm to 5 μm. The ultrafine electrospun fibers have a higher melt temperature than fibers derived by dry spinning.

Also provided are methods of making structures which include the ultrafine fibers, and may include any three-dimensional structure formed by weaving, knitting or laminating the ultrafine fibers or including the ultrafine fibers. A preferred embodiment is a nonwoven fabric. In a preferred embodiment the structure containing/including ultrafine fibers of P4HB and copolymers thereof has a thickness of from 0.05 mm to 5 mm.

DETAILED DESCRIPTION OF THE INVENTION

I. Definitions

"Absorbable" as generally used herein means the material is broken down in the body and eventually eliminated from the body within five years.

"Bioactive agent" is used herein to refer to therapeutic, prophylactic, and/or diagnostic agents. It includes without limitation physiologically or pharmacologically active substances that act locally or systemically in the body. A biologically active agent is a substance used for, for example, the treatment, prevention, diagnosis, cure, or mitigation of disease or disorder, a substance that affects the structure or function of the body, or pro-drugs, which become biologically active or more active after they have been placed in a predetermined physiological environment.

"Bicomponent" as generally used herein means a non-woven made of two or more materials.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer comprised of two or more different monomers.

"Copolymers of poly-4-hydroxybutyrate" as generally used herein means any polymer of 4-hydroxybutyrate with one or more different hydroxyl acid units.

"Light weight P4HB mesh" means a knitted mesh made from P4HB monofilament fiber with a fiber diameter of approx. 100 μm.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer of 4-hydroxybutyrate units. It may be referred to herein as P4HB or TephaFLEX® biomaterial (manufactured by Tepha, Inc., Lexington, Mass.).

"Regular weight P4HB mesh" means a knitted mesh made from P4HB monofilament fiber with a fiber diameter of approx. 165 μm.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

"Ultrafine fibers" as generally used herein means fibers having average diameters ranging from 10 nm to 10 μm.

II. Compositions

The compositions described therein are based on methods developed to produce medical devices containing ultrafine fibers of P4HB and copolymers thereof with high surface area to volume ratios. These methods may be used to prepare ultrafine fibers ranging in average diameter from 10 nm to 10 μm. The methods may be run continuously, which is particularly advantageous in manufacturing. The ultrafine fibers are prepared by electrospinning.

A major advantage of the method over thermal processing methods, such as melt blowing, is that the weight average molecular weight of the polymer may decrease less than 20% of its original value during electrospinning processing, more preferably less than 15%, and even more preferably less than 10%. In some embodiments, the weight average molecular weight of the polymer may decrease less than 5% of its original value during electrospinning, more preferably, less than 2% or its original value during electrospinning.

A major advantage of the method over conventional dry spinning is that the average diameter of the electrospun fibers is lower, the maximum fiber diameter of the electrospun fibers is substantially lower, the minimum fiber diameters of the electrospun fibers are in the nanometer range as opposed to the micron range i.e., although dry spinning produces fibers in the nanometer range, for a given sample, the fibers are predominantly in the micron range. By contrast, electrospun fibers size is predominantly in the nanometer range. The surface area to volume ratio (determined according using the formulae shown below) of the electrospun fibers is higher than dry spun or melt blown fibers.

Volume of fiber=$\pi r^2 h$

Surface area of fiber=$(2\pi rh)+(2\pi r^2)$ h=height or length of the fiber r=radius of the fiber The decrease in molecular weight loss is a particular advantage when it is desirable to retain mass and/or mechanical properties, such as burst strength, in vivo, for a prolonged period of time, since lower molecular weight P4HB non-wovens degrade faster in vivo than higher molecular weight P4HB non-wovens.

Electrospun fibers have a higher melt temperature (when compared to dry spun fibers) indicative of a higher degree of molecular orientation. Additionally, there is also less loss of polymer molecular weight when using electrospinning, as compared to dry spinning.

The electrospun ultrafine fibers of P4HB and copolymers thereof provided herein are biocompatible and can be used in medical applications, for example, as implants such as devices for soft and hard tissue repair, replacement, and regeneration, temporary tissue support, tissue separation, as well as devices or components of devices for tissue in-growth (or guided tissue regeneration) and tissue engineering.

A. Polymers

The ultrafine fibers are formed of poly-4-hydroxybutyrate (P4HB) or a copolymer thereof. Copolymers include P4HB with another hydroxyacid, such as 3-hydroxybutyrate, and P4HB with glycolic acid or lactic acid monomer. P4HB and copolymers thereof can be obtained from Tepha, Inc. of Lexington, Mass.

In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred in order to improve the strength of the fiber. The viscosity of the polymer solution may also be tailored by varying the molecular weight of the P4HB homopolymer and copolymers thereof (as well as varying the solvent system).

If desired, the PHA polymers may be blended or mixed with other materials prior to electrospinning provided the melting point of the blend is greater than body temperature.

In a particularly preferred embodiment, P4HB and its copolymers may be blended with other absorbable polymers. Examples of other absorbable polymers include, but are not limited to, polymers containing glycolic acid, lactic acid, 1,4-dioxanone, trimethylene carbonate, 3-hydroxybutyric acid, caprolactone, including polyglycolic acid, polylactic acid, polydioxanone, polycaprolactone, copolymers of glycolic and lactic acids such as VICRYL® polymer, and the MAXON® and MONOCRY® polymers. The ratio of the PHA polymer in the blend to the non-PHA polymer component(s) may be varied in order to select the desired properties of the ultrafine fibers, and to ensure the melting point of the electrospun ultrafine fibers is greater than body temperature.

The P4HB homopolymer and copolymers thereof may also be blended with other polymers, such as polyethylene oxide, polypropylene oxide, polyoxyethylene-polypropylene oxide block copolymers ("PLURONICS®", BASF), as well as other components prior to electrospinning Other components which can be added to the electrospun polymer include, but are not limited to, surfactants, water-soluble polymers, organic or inorganic powders including fillers and bioceramics. Particularly preferred bioceramics are degradable, and include tricalcium phosphate (α and β forms of TCP—with a nominal composition of $Ca_3(PO_4)_2$), biphasic calcium phosphate (BCP), calcium sulfate, calcium carbonate, hydroxyapatite and other calcium phosphate salt-based bioceramics. Bio-active glasses may also be incorporated prior to electrospinning. If desired, plasticizers, nucleants, dyes, compatibilizers, and other additives may also be added to the P4HB and copolymers thereof. U.S. Pat. No. 6,905,987 to Noda et al. discloses examples of plasticizers.

It may also be advantageous to incorporate contrast agents, radiopaque markers, or radioactive substances into the polymer compositions. Alternatively, these can be incorporated into structures containing or made of the ultrafine fibers.

B. Ultrafine Fibers

It has been discovered that structures of ultrafine fibers can be prepared by electrospinning with high surface area to volume ratios. These ultrafine fibers have higher melting points than fibers derived by dry spinning. In a preferred embodiment, ultrafine fibers of P4HB and copolymers thereof can be prepared by electrospinning with an average diameter of 10 nm to 10 μm and more preferably from 50 nm to 5 μm. In contrast, fibrous structures of P4HB and copolymers thereof produced by melt blowing and dry spinning (see for example WO 2011/159784 to Cahil et al.) incorporate larger diameter fibers with average diameters of up to, for example, 50 μm, and therefore have lower surface area to volume ratios than structures produced by electrospinning. The lower average diameter of the ultrafine fibers produced by electrospinning is a major advantage in medical applications where a higher surface area to volume ratio is desirable. For example, a higher surface area is desirable in tissue engineering applications where cell attachment increases with surface area. The ability to vary the surface area to volume ratio is also a major advantage in controlling the in vivo degradation rate of an implant made from the ultrafine fibers since it is known that P4HB and copolymers degrade by surface erosion as well as bulk hydrolysis (see Martin, D. et al. Medical Applications of Poly-4-hydroxybutyrate: A Strong Flexible Absorbable Biomaterial, *Biochem. Eng. J.* 16:97-105 (2003)).

The ultrafine fibers with average diameters ranging from 10 nm to 10 μm can be prepared by appropriate choice of (i) solvent and solution properties, such as viscosity, conductivity, evaporation rate, concentration and surface tension, (including selection of polymer molecular weight) (ii) equipment set up conditions, such as the distance between the spinneret and collector plate, the electric potential applied, and the pressure or flow rate of the polymer material solution, (iii) atmospheric conditions, such as temperature, humidity, and any applied air velocity between the spinneret and collector plate, and (iv) polymer properties such as Mw, composition, melting properties, thermal properties and crystallization rate.

Ultrafine fibers of P4HB and copolymers thereof can be prepared by electrospinning with unexpectedly high retention of polymer weight average molecular weight. Notably, the weight average molecular weight of the polymer decreases less than 20% during electrospinning, more preferably less than 15%, and even more preferably less than 10%. In contrast, melt blown fibers of P4HB and copolymers thereof typically lose a significant amount of the polymer's initial molecular weight during melt processing. WO 09/085823 to Ho et al., for example, describes methods to produce melt blown fibers of P4HB and copolymers thereof by melt processing wherein the polymer loses 47-52% of the polymer's initial molecular weight.

In addition to providing fibers with higher surface area, another major advantage of the electrospinning method over dry spinning is that the electrospun fibers have higher melting points. This is thought to be due to the higher orientation of the fibers that can be achieved during electrospinning versus dry spinning Since it is known that increased molecular orientation results in increased tensile strength of fibers of P4HB and copolymers thereof (see Martin, D. et al. Medical Applications of Poly-4-hydroxybutyrate: A Strong Flexible Absorbable Biomaterial, *Biochem. Eng. J.* 16:97-105 (2003)), electrospinning produces fibers with higher tensile strength than dry spinning Higher tensile strength of ultrafine fibers of P4HB and copolymers thereof is important in medical applications where not only high initial strength is required at the time of implantation, but also when prolonged strength retention is necessary since a higher degree of orientation slows polymer degradation in vivo and improves strength retention. For example, prolonged strength retention is important in the reinforcement of repaired tissues.

Higher melt temperatures of the ultrafine fibers is also an advantage because it makes products derived from them, such as medical devices, less sensitive to increases in temperature. Exposure of thermoplastic materials, such as P4HB, to increases in temperature can result in significant undesirable changes in physical properties, such as warpage or shrinkage, without any associated phase change. Increasing the melt temperature consequently reduces the onset or extent of these physical changes. For example, a higher melt temperature of the ultrafine fibers can eliminate the need for refrigeration during product shipment, and also the need for temperature indicators to be included with the products. Thus, products derived from ultrafine fibers can be shipped through hot climates without risk that the product will be melted, warped or otherwise harmed in the absence of expensive refrigeration. Furthermore, since the glass transition of P4HB is approximately −51° C. and the melt temperature of bulk P4HB is approximately 58-60° C., raising the melt temperature of P4HB fibers decreases the sensitivity of the polymer to physical changes upon implantation into the body where the temperature is 37° C.

In some embodiments, the ultrafine fibers may be crosslinked. The polymer may be derivatized using chemical agents or gas plasma to introduce new functional groups prior to cross-linking. Suitable crosslinking agents include, but are not limited to: bifunctional crosslinking agents reactive toward hydroxyl and/or carboxylic acid groups. Representative covalent crosslinking agents include carbodiimides and diisocyanates. In certain embodiments, the covalent crosslinking agent is selected from epichlorohydrin, gluteraldehyde, hexamethylene diisocyanate, adipic acid hydrazide, and 1-ethyl-3-(3-dimethylaminopropyl) carbodiimide hydrochloride. Crosslinking of the polymer may also be achieved through exposure to radiation such as gamma irradiation or ultraviolet light or generation of free radicals.

C. Structures Containing Ultrafine Fibers

The structures include at least the aforementioned ultrafine fibers, but a structure may also include any three-dimensional structure formed by weaving, knitting or laminating the ultrafine fibers or including the ultrafine fibers. A preferred embodiment is a nonwoven fabric.

In a preferred embodiment the structure containing ultrafine fibers of P4HB and copolymers thereof has a thickness of from 0.05 mm to 5 mm.

The percentage of ultrafine fibers of P4HB and copolymers thereof in the structure is not particularly limited, but is preferably 20 wt % or more. A particularly preferred structure is composed essentially of only ultrafine fibers of P4HB and copolymers thereof.

The structure resulting from the electrospinning process may be used alone or in combination with other structural components. For example, the structure of ultrafine fibers may be combined or laminated with a nonwoven fabric, woven fabric, knitted mesh or film. Alternatively the ultrafine fibers can be deposited directly on another material by using it as the collecting plate. For example, a laminate or bicomponent material can be directly formed by electrospraying ultrafine fibers of P4HB and copolymers thereof onto support structures such as a nonwoven fabric, woven fabric, knitted mesh, foam, or film.

In a particularly preferred embodiment, the ultrafine fibers are electrospun onto a: P4HB monofilament mesh, a P4HB multifilament mesh, a P4HB nonwoven fabric, a P4HB woven fabric, a P4HB foam, or a P4HB film, and any combinations thereof. In an even more preferred embodiment, the ultrafine electrospun fibers cover more than 10% of the surface area of the P4HB monofilament mesh, a P4HB multifilament mesh, a P4HB nonwoven fabric, a P4HB woven fabric, a P4HB foam, or a P4HB film, and any combinations thereof.

In another embodiment, bicomponent structures may be prepared by electrospinning two or more different materials simultaneously from either the same solution or from different spinnerets.

Three-dimensional structures containing electrospun ultrafine fibers may also be formed by using moving spinnerets or nozzles, and by using moving collector plates, including other moving structural shapes used as collector plates.

The structures containing ultrafine fibers of P4HB and copolymers thereof may be subjected to further modification. These include heat treatments, chemical treatments, surface treatments, and or gas plasma treatments.

A significant advantage of using electrospinning instead of melt blowing to produce webs of ultrafine fibers of P4HB and copolymers thereof is that the process can be controlled to allow the formation of webs with unexpectedly high cohesion of the fibers. This is achieved by controlling the solvent evaporation rate in order to collect fibers that briefly remain tacky thereby improving the fusion of the ultrafine fibers at their crossover points. The higher cohesion of the fibers, preferably combined with ultrafine fibers having higher degrees of orientation, results in webs with improved mechanical properties, such as burst strength.

D. Other Components

The structures may comprise other components. These other components may either be incorporated at the time of electrospinning or after the electrospinning process.

Therapeutic, Diagnostic or Prophylactic Agents

Bioactive agents include biologically, physiologically, or pharmacologically active substances that act locally or systemically in the human or animal body. Examples can include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, peptides, proteins, antibodies, growth factors, fibronectin, laminin, vitronectin, integrins, antibiotics, steroids, hydroxyapatite, silver particles, vitamins, non-steroidal anti-inflammatory drugs, chitosan and derivatives thereof, alginate and derivatives thereof, collagen, sugars, polysaccharides, nucleotides, oligonucleotides, lipids, hyaluronic acid and derivatives thereof, antisense molecules, aptamers, siRNA, nucleic acids, and combinations thereof.

In one embodiment, the ultrafine fiber structures can comprise proteins, peptides, sugars, polysaccharides, glycoproteins, lipids, lipoproteins, nucleic acid molecules, inorganic or organic synthetic molecules, or combinations thereof. In a preferred embodiment, the structures comprise growth factors, fibronectin, laminin, vitronectin, integrins, hyaluronic acid and derivatives thereof, chitosan, nucleic acid molecules, antisense molecules, steroids, anesthetics, hormones, anti-inflammatory agents, immunomodulatory agents, molecules that promote cell migration, molecules that promote cell division, molecules that promote cell proliferation and differentiation, molecules that stimulate phenotypic modification of cells, molecules that promote angiogenesis, molecules that promote vascularization, molecules that promote extracellular matrix disposition, allograft material, xenograft material, and hyaluronic acid and derivatives thereof. The structures may also be seeded with cells to improve tissue ingrowth and healing. In a particularly preferred embodiment, the structures comprise signaling ligands, including members of the TGF-beta family, bone morphogenic proteins, fibroblast growth factors-1 and -2, plateletderived growth factor-AA and -BB, and platelet rich plasma and vascular endothelial cell-derived growth factor.

In yet another preferred embodiment the structures may be used for the controlled release of drugs, or incorporate systems for the controlled release of drugs.

Wetting Agents

Wetting agents designed to improve the wettability of the surfaces of the structures containing the ultrafine fibers may also be incorporated in order to allow fluids to be easily adsorbed onto the implant surfaces, and to promote cell attachment. Examples of wetting agents include polymers of ethylene oxide and propylene oxide, such as polyethylene oxide, polypropylene oxide, or copolymers of these, such as pluronics. Other wetting agents may be surfactants or emulsifyers.

Surface Coatings

If desired, the structures may be coated with a ceramic, preferably a resorbable ceramic. Resorbable bioceramics that can be used must: (i) be biocompatible, (ii) eventually be resorbed by the body, and (iii) permit the replacement or repair of damaged tissues in the body. Examples of resorbable bioceramics include tricalcium phosphate (α and β forms of TCP—with a nominal composition of $Ca_3(PO_4)_2$), biphasic calcium phosphate (BCP), calcium sulfate, hydroxylapatite, calcium carbonate, and other calcium phosphate saltbased bioceramics. Bio-active glasses may also be incorporated into the structures. Bioactive glasses are composed of $SiO_2$, Na2O, CaO and $P_2O_5$ in specific proportions.

E. Formation into Devices

Structures made from P4HB polymers and copolymers thereof by electrospinning processes are characterized by their formation from ultrafine fibers with average diameters ranging from 10 nm to 10 μm. Notably, the electrospun derived structures may be produced with smaller average diameter fibers than structures produced by either melt-blowing or dry spinning. The electrospun structures prepared from ultrafine fibers are characterized by their high surface area to volume ratio. The structures may also comprise ultrafine fibers with higher melt temperatures than those derived by dry spinning. The structures made by electrospinning also comprise ultrafine fibers where the weight average molecular weight of the polymer has decreased less than 20%, more preferably less than 15%, and even more preferably less than 10% of its original value during electrospinning.

The electrospun structures have properties that are substantially improved for many medical applications relative to glycolic and lactic acid derived electrospun structures. While structures derived from polymers of glycolic and lactic acids release acidic monomers, electrospun structures derived from P4HB and copolymers thereof release much less acidic degradation products since the 4-hydroxybutyric acid monomer is less acidic (i.e. has a higher pKa) than that of glycolic and lactic acids. The electrospun structures derived from P4HB and copolymers thereof will also retain strength longer in vivo due to the slower degradation of these polymers in vivo, and therefore the structures will retain their integrity for longer. This is important where healing requires a prolonged period, and is particularly important where the electrospun structure is in the form of a scaffold for tissue engineering which needs to be present for an extended period to allow time for tissue in-growth and tissue maturation.

The electrospun ultrafine fibers may be used to prepare structures that are suitable for use as medical devices. In particular, structures can be formed for use as implantable medical devices. For example, the structures containing ultrafine fiber made from P4HB and copolymers thereof may be used to make partially or fully absorbable biocompatible medical devices, or components thereof. Such devices include, but are not limited to: stent, stent graft, drug delivery device, device for temporary wound or tissue support, device for soft or hard tissue repair or regeneration, repair patch, tissue engineering scaffolds, retention membranes (for example, to retain bone graft), anti-adhesion membrane, tissue separation membrane, surgical mesh (including mesh for face lift, neck lift, eyebrow lift, breast lift, or breast reconstruction), hernia repair device, cardiovascular patch, vascular closure device, sling, rotator cuff repair device, meniscus repair device, guided tissue repair/regeneration device, articular cartilage repair device, osteochondral repair device, bone void filler, nerve guide, tendon repair device, intracardiac septal defect repair device, including but not limited to atrial septal defect repair devices and patent foramen ovale (PFO) closure devices, left atrial appendage (LAA) closure device, pericardial patch, bulking and filling agent, vein valve, heart valve, bone marrow scaffold, meniscus regeneration device, ligament and tendon graft, spinal fusion device, skin substitute, wound healing device, dural substitute, bone graft substitute, wound dressing, ulcer repair device, and a hemostat.

III. Methods of Manufacturing Ultrafine Fibers of P4HB and Copolymers Thereof and Three Dimensional Structures Methods are provided for manufacturing ultrafine fibers of P4HB and Copolymers as well as three dimensional structures containing the ultrafine fibers, by electrospinning.

Figure 1:
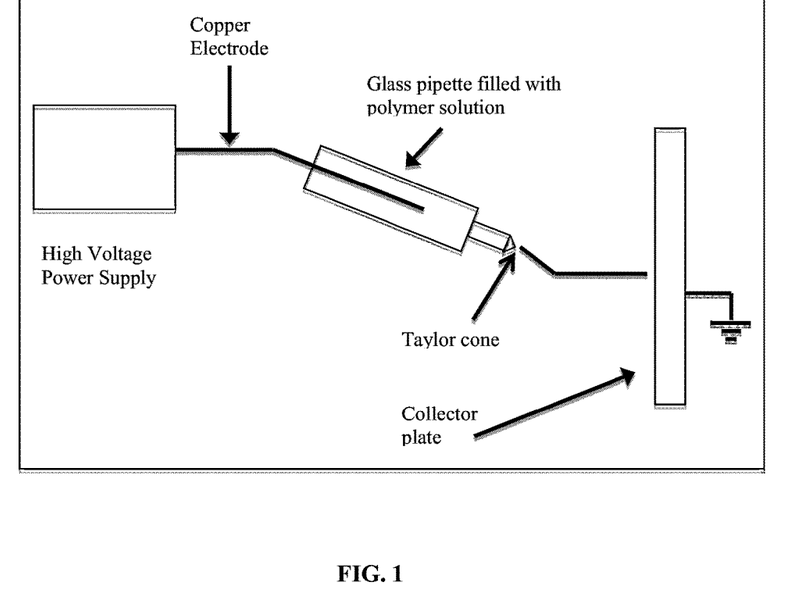
FIG. 1 is a diagram of the process to manufacture ultrafine fibers from poly-4-hydroxybutyrate and copolymers thereof by electrospinning.

A. Method of Making P4HB Polymer or Copolymer Ultrafine Fibers by Electrospinning In a preferred method, ultrafine fibers of P4HB polymer or copolymer thereof may be prepared as follows. The P4HB polymer or copolymer is dissolved in a solvent to make a polymer solution. A suitable electrospinning apparatus is shown in FIG. 1, and consists of a high voltage power supply with a positive lead connected to a copper wire. The copper wire is inserted into a nozzle, such as a glass capillary, from which the polymer solution is electrospun. The glass capillary is either filled with the polymer solution, or alternatively the polymer solution can be pumped through the capillary (with for example a precision pump). A collector is positioned at a desired distance from the nozzle or capillary, and the collector is connected to the negative lead (i.e. ground) of the power supply. Charged jets of polymer are consistently shot to the collector due to the applied electrical potential. Solvent evaporates during the time the jet of polymer hits the collector due to the high surface to volume ratio of the strands coupled with the humidity and temperature.

A number of parameters can be varied to control the sizes of the ultrafine fibers. These include, but are not limited to, solution flow rate (ml/min), distance between the nozzle and the collector, needle configuration (including needle diameter and needle extrusion distance), temperature, humidity, choice of solvent, polymer molecular weight, collection time, electric potential, and use of compressed gas to attenuate the fibers.

In a preferred embodiment, ultrafine fibers of P4HB and copolymers thereof are prepared from solutions with polymer concentrations preferably from 1 to 30 wt %, and more preferably 2 to 25 wt %. There are no particular restrictions on the solvent that can be used except it must be capable of dissolving the P4HB and copolymers thereof, and evaporate during the spinning stage to allow the formation of the electrospun ultrafine fibers. If necessary, reduced pressure conditions can be used during the fiber drawing stage if the solvent evaporation is insufficient, as well as temperatures ranging from 0-100° C. that are selected according to the evaporation behavior of the solvent and stability of the polymer. Volatile solvents that are liquid at room temperature, and have boiling points no higher than 200° C. are particularly preferred. Examples of volatile solvents include methylene chloride, chloroform, dichloroethane, tetrachloroethane, trichloroethane, dibromomethane, bromoform, acetone, acetonitrile, tetrahydrofuran, 1,4-dioxane, 1,1,1,3,3,3-hexafluoroisopropanol, toluene, xylene, dimethylformamide (DMF), and dimethylsulfoxide. These solvents may be used alone, or two or more solvents may be combined for use as a mixed solvent system. Particularly preferred solvents include methylene chloride, chloroform, dichloroethane, tetrachloroethane, trichloroethane, dibromomethane, bromoform, tetrahydrofuran, acetone, dimethylformamide, and 1,4-dioxane.

In a preferred embodiment, the applied electrostatic potential required to form the ultrafine fibers will normally be 3-100 kV, preferably 5-50 kV, and more preferably 5-30 kV. The distance between the spinneret and collector plate to form the ultrafine fibers will be dependent upon the charge, spinneret dimensions, ejection volume, and polymer concentration. A distance of 5-30 cm is normally suitable when the electrostatic potential is close to 5-30 kV. A relative humidity of 20-80% is generally preferred in order 30 to achieve stable spinning conditions. More preferably the relative humidity should be 30-70%.

B. Method of Making Three-Dimensional P4HB Polymer or Copolymer Structures by Electrospinning A particular advantage of the electrospinning method over melt blown methods is that the ultrafine fibers can be spun directly onto scaffolding structures. The method may also be used to make three-dimensional structures.

This is achieved by either positioning the scaffold at the fiber collection plate and rotating the scaffolding structure during fiber collection, or alternatively, rotating the nozzle around the scaffold. Alternatively, the electric field may be changed to alter the deposition of the spun fibers.

In a preferred embodiment, the ultrafine fibers are electrospun onto a collector that has been sprayed or coated with an anti-static agent, such as static guard. The use of an anti-static (or conductive) coating can alter the deposition of the ultrafine fibers on the collector plate, and improve the coating of the collector material with the ultrafine fibers. In a particularly preferred embodiment, the ultrafine fibers are electrospun onto the following collectors that have been sprayed or coated with an anti-static (or conductive) coating: P4HB monofilament mesh, a P4HB multifilament mesh, a P4HB nonwoven fabric, a P4HB woven fabric, a P4HB foam, or a P4HB film, or any combinations thereof. One particular advantage of using an anti-static agent to coat these collector materials is that it allows the ultrafine fibers to become in intimate contact with these collector materials, for example, invading pores of meshes, fabrics and foams. This results in a greater proportion of the substrate being covered by the ultrafine fibers, and is particularly useful in the preparation of scaffolds for tissue repair and regeneration. In a particularly preferred embodiment, the ultrafine fibers cover more than 25% of the surface area of the collector material (such as a P4HB monofilament mesh, a P4HB multifilament mesh, a P4HB nonwoven fabric, a P4HB woven fabric, a P4HB foam, or a P4HB film) that has been treated with an anti-static agent.

The present invention will be further understood by referenced to the following non-limiting examples.

EXAMPLES

Example 1: Preparation of Ultrafine Fibers of P4HB by Electrospinning with Low Molecular Weight Polymer P4HB (Tepha, Inc., Lexington, Mass.) (Mw 109 kDa) was dissolved in a solvent or solvent mixture as shown in Table 1. Ultrafine fibers of P4HB were produced as described above, using the conditions shown in Table 1 for solvents, polymer solution concentration, voltage, distance between the capillary needle and collector plate, time of collection, and collector type. The electrospun ultrafine fibers were collected under ambient conditions of temperature and humidity. The temperature was 27° C. (81° F.), and the relative humidity (RH) was 57%.

TABLE 1

| Sample | Solvent | Polymer Conc. (wt/vol %) | Voltage (kV) | Needle to collector distance | Time of collection (min) | Nature of collector |
|---|---|---|---|---|---|---|
| A1 | $CHCl_3$ | 20 | 11 | 3 in (7.62 cm) | 5 | Al pan |
| A2 | $CHCl_3$ | 20 | 11 | 4.5 in (11.43 cm) | 5 | Al pan |
| A3 | $CHCl_3$ | 20 | 11 | 6 in (15.24 cm) | 5 | Al pan |
| A4 | $CHCl_3$ | 20 | 11 | 10 in (25.4 cm) | 15 | Al pan |
| A5 | $CHCl_3$ | 20 | 11 | 6 in (15.24 cm) | 5 | Steel screen |
| A6 | $CHCl_3$ | 20 | 11 | 6 in (15.24 cm) | 5 | Light weight P4HB mesh |
| A7 | $CHCl_3$/DMF (50:50) | 10 | 22 | 4 in (10.16 cm) | 5 | Steel screen |
| A8 | $CHCl_3$/DMF (50:50) | 10 | 22 | 6 in (15.24 cm) | 5 | Steel screen |
| A9 | $CHCl_3$/DMF (50:50) | 10 | 11 | 6 in (15.24 cm) | 5 | Steel screen |

Example 2: Preparation of Ultrafine Fibers of P4HB by Electrospinning with High Molecular Weight Polymer P4HB (Tepha, Inc., Lexington, Mass.) (Mw 401 kDa) was dissolved in a solvent or solvent mixture as shown in Table 2. Ultrafine fibers of P4HB were produced as described in the methods above using the conditions shown in Table 2 for solvents, polymer solution concentration, voltage, distance between the capillary needle and collector plate, time of collection, and collector type. The electrospun ultrafine fibers were collected under ambient conditions of temperature and humidity. The temperature was 27° C. (81° F.), and the relative humidity (RH) was 57%.

In the cases of samples B8-B13, the ultrafine fibers were collected directly on a P4HB mesh. In the cases of samples B12 and B16, where the collectors were a regular weight P4HB mesh and a steel screen, the collectors were sprayed with static guard prior to the collection of the ultrafine fibers.

TABLE 2

| Sample | Solvent | Polymer Conc. (wt/vol %) | Voltage (kV) | Needle to collector distance | Time of collection (min) | Nature of collector |
|---|---|---|---|---|---|---|
| B1 | CHCl$_3$ | 5 | 17 | 6.5 in (16.51 cm) | 5 | Steel screen |
| B2 | CHCl$_3$ | 5 | 5 | 6.5 in (16.51 cm) | 5 | Steel screen |
| B3 | CHCl$_3$/DMF (50:50) | 10 | 11 | 5 in (12.7 cm) | 5 | Steel screen |
| B4 | CHCl$_3$/DMF (50:50) | 10 | 11 | 5 in (12.7 cm) | 10 | Steel screen |
| B5 | CHCl$_3$/DMF (50:50) | 10 | 11 | 5.5 in (13.97 cm) | 5 | Steel screen |
| B6 | CHCl$_3$/DMF (50:50) | 10 | 11 | 4.5 in (11.43 cm) | 5 | Al pan |
| B7 | CHCl$_3$/DMF (50:50) | 10 | 11 | 4.5 in (11.43 cm) | 5 | Steel screen |
| B8 | CHCl$_3$/DMF (50:50) | 10 | 11 | 4.5 in (11.43 cm) | 5 | Light weight P4HB mesh |
| B9 | CHCl$_3$/DMF (50:50) | 10 | 11 | 4.5 in (11.43 cm) | 2 | Light weight P4HB mesh |
| B10 | CHCl$_3$/DMF (50:50) | 10 | 11 | 4.5 in (11.43 cm) | 5 | Regular weight P4HB mesh |
| B11 | CHCl$_3$/DMF (50:50) | 10 | 11 | 4.5 in (11.43 cm) | 2 | Regular weight P4HB mesh |
| B12 | CHCl$_3$/DMF (50:50) | 10 | 11 | 4.5 in (11.43 cm) | 5 | Regular weight P4HB mesh with static guard |
| B13 | CHCl$_3$/DMF (50:50) | 10 | 11 | 4.5 in (11.43 cm) | 5 | Regular weight P4HB mesh |
| B14 | CHCl$_3$/DMF (50:50) | 50 | 11 | 5 in (12.7 cm) | 5 | Steel screen |
| B15 | CHCl$_3$/DMF (50:50) | 50 | 11 | 5 in (12.7 cm) | 2 | Steel screen |
| B16 | CHCl$_3$/DMF (50:50) | 50 | 11 | 5 in (12.7 cm) | 5 | Steel screen static guard |
| B17 | CHCl$_3$/DMF (50:50) | 50 | 11 | 5 in (12.7 cm) | 5 | Al pan |

Ultrafine fibers of high molecular weight P4HB (B8 of Table 2) were collected on a light-weight P4HB monofilament mesh as described herein. Notably, the ultrafine fibers laminated the surface of the mesh without any significant penetration into the pores of the mesh.

Ultrafine fibers of high molecular weight P4HB (Sample B12 of Table 2) were collected on a regular weight P4HB monofilament mesh that had been treated with a static guard spray. Notably, the results obtained were in contrast to Sample B8. In the case of Sample B12, treatment of the P4HB mesh with an anti-static spray resulted in an intimate contact of the ultrafine fibers with the P4HB mesh, and penetration into the pores of the mesh by the ultrafine fibers. Consequently, the use of the anti-static spray results in a larger proportion of the P4HB mesh being covered by the ultrafine fibers, and an improved cohesion of the fibers with the coated substrate.

Example 3: Comparison of Fiber Molecular Weight Derived by Electro Spinning Versus Melt Blowing The molecular weight Mw of a sample of the electrospun ultrafine fibers of Table 1 (low molecular weight P4HB—Sample A7) was determined by GPC relative to polystyrene, and found to be 107 kDa. Therefore the low molecular weight P4HB polymer lost a Mw of only 2 kDa (or approx. 1.8%) during processing into the ultrafine fibers of Sample A7.

The molecular weight Mw of a sample of the electrospun ultrafine fibers of Table 2 (high molecular weight P4HB—Sample B6) was determined by GPC relative to polystyrene, and found to be 383 kDa. Therefore the high molecular weight P4HB polymer lost a Mw of only 18 kDa (or approx. 4.5%) during processing into the ultrafine fibers of Sample B6. The molecular weight Mw of Sample B14 shown in Table 2 was also determined by GPC relative to polystyrene, and found to be 364 kDa representing a loss of P4HB Mw of 37 kDa (or approx. 9.2%) on electrospinning.

For comparison, the molecular weight drop of several samples of P4HB melt-blown non-woven fibers prepared according to the procedure of Example 1 of WO 09/085823 to Ho et al. using P4HB with a starting molecular weight (Mw) of 328 kDa were determined. The molecular weight (Mw) of the resulting P4HB melt-blown non-woven fibers were found to be 207 to 157 kDa, representing a 47 to 52% decrease in the molecular weight (Mw) of the polymer during processing.

Example 4: Comparison of the Melt Temperature of Electrospun Fibers Versus Dry Spun Fibers Melting points of electrospun and dry spun fibers were determined for comparison with a differential scanning calorimeter (DSC, Perkin Elmer Pyris 1), and the melting points were determined from the isothermal peaks. The melt temperature (Tm) of the electrospun ultrafine fibers of Table 2 (high molecular weight P4HB—Sample B14) was determined by differential scanning calorimetry, and found to be 60.78° C.

For comparison, the melt temperature (Tm) of a sample of P4HB dry spun non-woven prepared according to Example 1 of the procedure of WO 2011/159784 to Cahil et al. was determined. The melt temperature (Tm) of the fibers of the dry spun was found to be 59.18° C., which is 1.6° C. lower than the melt temperature (Tm) of the electrospun ultrafine fibers.

Figure 2A:
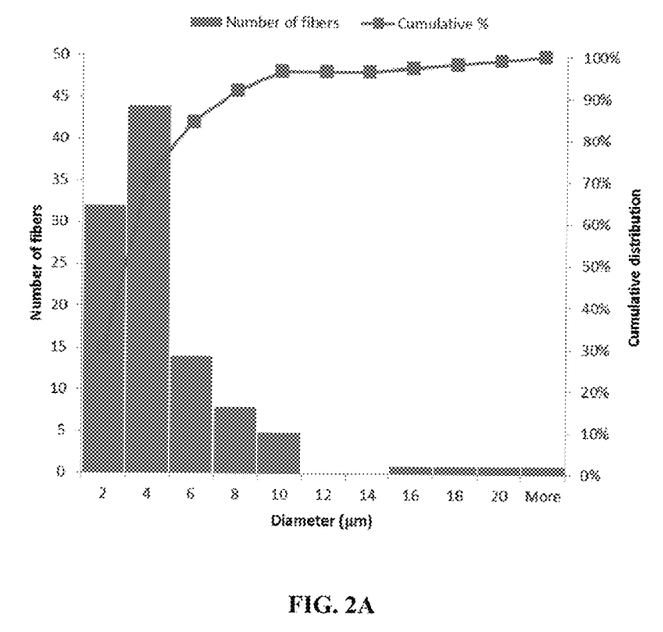
FIGS. 2A-2C show the fiber diameters for fibers made by dry spinning (2A), melt blowing (2B) and electrospinning (2C).

Example 5: Comparison of Average Diameter of Electrospun Fibers, Melt Blown Fibers and Dry Spun Fibers Several samples of P4HB (Mw=490 kDa) dry spun fibers were prepared according to the procedure in Example 1 of WO 2011/159784 to Cahil et al. The mean fiber diameter of these dry spun fibers was measured by selecting 108 random locations from a photograph taken of the surface of the fiber structure at high magnification using a scanning electron microscope, and the average value of the fiber diameters (n=108) was determined and recorded as the fiber mean diameter. The fiber mean diameter was found to be 4.0 μm with a standard deviation of 4.3 μm. The minimum fiber diameter measured was 0.92 μm, and the maximum fiber diameter measured was 36.8 μm. The fiber diameter distribution is shown in FIG. 2A.

Figure 2B:
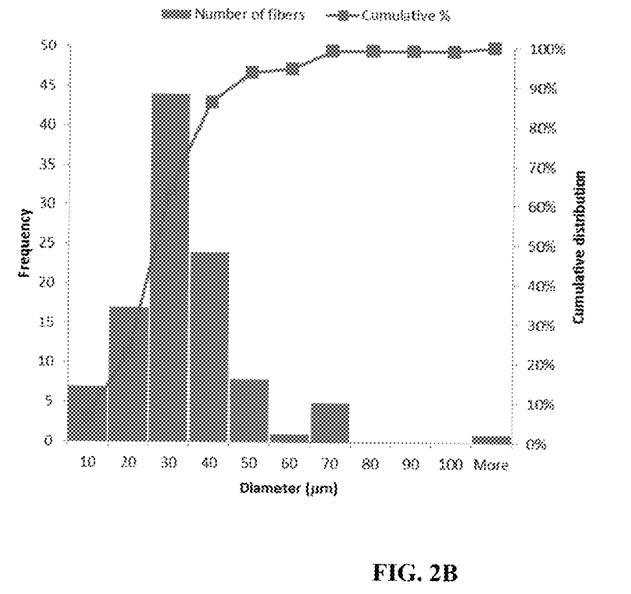

A sample of P4HB (Mw=328 kDa) melt blown fibers was prepared according to the procedure of U.S. Pat. No. 8,287,909 to Martin et al. The same procedure as described above (namely selecting 108 random locations of a SEM picture of the melt-blown fibers) was used to determine the mean fiber diameter of the meltblown fibers. The fiber mean diameter of the melt-blown fibers was found to be 28.9 μm with a standard deviation of 16.6 μm. The minimum fiber diameter measured was 5.6 μm, and the maximum fiber diameter measured was 141 μm. The fiber diameter distribution is shown in FIG. 2B.

The same procedure was used to determine the fiber mean diameter of the electrospun fibers (P4HB, Mw=401 kDa) prepared in Example 1. The fiber mean diameter was found to be 1.64 μm with a standard deviation of 0.97 μm. The minimum fiber diameter measured was 620 nm, and the maximum fiber diameter measured was 5.3 μm. The dimensions of the P4HB fibers derived by electrospinning, melt blowing and dry spinning are summarized in Table 3 for comparison.

TABLE 3

| Sample | Mean fiber diameter (μm) | Standard deviation (μm) | Minimum fiber diameter (μm) | Maximum fiber diameter (μm) |
| --- | --- | --- | --- | --- |
| Electrospun fibers | 1.64 | 0.97 | 0.62 | 5.3 |
| Dry spun fibers | 4.00 | 4.30 | 0.92 | 36.8 |
| Melt-blown fibers | 28.9 | 16.6 | 5.60 | 141.0 |

Figure 2C:
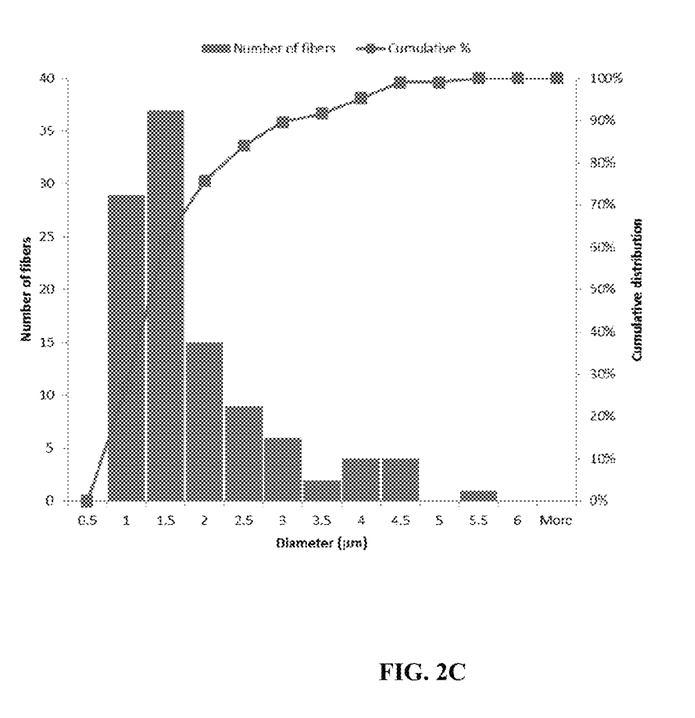

This example demonstrates that the electrospun fibers made from high molecular weight P4HB have a significantly lower mean fiber diameter than the melt-blown fibers and the dry spun fibers. The electrospun fibers also have lower minimum and maximum diameter values than the melt-blown and dry spun fibers. Furthermore, although the dry spinning technique can produce fibers with diameters as low as about 1 μm (the minimum fiber diameter), the maximum diameters of the dry spun fibers are about 7× larger than the electrospun fibers. This example also demonstrates that the standard deviation of the mean fiber diameter of the electrospun fibers is much lower than the standard deviation of the mean fiber diameter for the dry spun fibers. As such, the surface area to volume ratio of the electrospun fibers is much higher than the dry spun fibers and the meltblown fibers. The diameter distribution for fibers made using dry spinning is shown in FIG. 2C. The lower molecular weight P4HB (Mw=109 kDa) yielded electrospun fibers with an average diameter of 5.19 microns with a standard deviation of 2.16 microns.

Example 6: Preparation of Ultrafine fibers of Poly-4-hydroxybutyrate-co-3-hydroxybutyrate Copolymer (PHA3444) by Electrospinning Ultrafine fibers of PHA3444 may be prepared by dissolving the P4HBco-3HB (PHA3444) copolymer in a solvent or solvent mixture as shown in Table 2. Ultrafine fibers of PHA3444 may be electrospun as described in methods above using the conditions shown in Table 2 for solvents, polymer solution concentration, voltage, distance between the capillary needle and collector plate, time of collection, and collector type. The electrospun ultrafine fibers may be collected under ambient conditions of temperature and humidity.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An ultrafine non-woven web of polymeric fibers comprising a polymer, and optionally, an additive, wherein the polymer is selected from the group consisting of:
   (a) poly-4-hydroxybutyrate (P4HB) homopolymer; and
   b) a blend of P4HB homopolymer with a polymer selected from the group consisting of polymers derived from glycolic acid and lactic acid;
   wherein the ultrafine fibers are produced by electrospinning,
   wherein the non-woven does not include laminin,
   wherein the fibers have an average diameter of from 10 nm to 10 μm;
   wherein the weight average molecular weight of the poly-4-hydroxybutyrate homopolymer decreases less than 10% during the processing of the homopolymer into the electrospun ultrafine fibers; and
   wherein the maximum diameter of the fibers does not exceed 25 μm.

2. The ultrafine fibers of claim 1 wherein the fibers have a fiber diameter less than 900 nm.

3. The ultrafine fibers of claim 1 wherein the poly-4-hydroxybutyrate homopolymer has a weight average molecular weight greater than 50 kDa relative to polystyrene.

4. The ultrafine fibers of claim 1 wherein the ultrafine fibers have a melt temperature of at least 60° C.

5. The ultrafine fibers of claim 1 wherein the ultrafine fibers have been deposited on a P4HB monofilament mesh, a P4HB multifilament mesh, a P4HB nonwoven fabric, a P4HB woven fabric, a P4HB foam, or a P4HB film.

6. The ultrafine fibers of claim 1 wherein the melt temperature of the ultrafine fibers is greater than body temperature, or wherein the structure has been crosslinked either covalently or non-covalently.

7. The ultrafine fibers of claim 1 further comprising a bioactive agent.

8. The ultrafine fibers of claim 1 wherein the additive is selected from the groups consisting of plasticizers, nucleants, compatibilizers, porogens, radiolabelled substances, imaging agents, radiopaque markers, contrast agents, antioxidants, and dyes.

9. A medical device comprising the ultrafine fibers of claim 1.

10. The device of claim 9, wherein the ultrafine fibers are electrospun directly onto a scaffold or other substrate to form the device.

11. The device of claim 10 wherein the device is selected from the group consisting of a stent, stent graft, drug delivery device, device for temporary wound or tissue support, device for soft or hard tissue repair or regeneration, repair patch, tissue engineering scaffolds, retention membranes, anti-adhesion membrane, tissue separation membrane, hernia repair device, cardiovascular patch, vascular closure device, sling, rotator cuff repair device, meniscus repair device, guided tissue repair/regeneration device, articular cartilage repair device, osteochondral repair device, bone void filler, nerve guide, tendon repair device, intracardiac septal defect repair device, atrial septal defect repair devices, patent foramen ovale (PFO) closure devices, left atrial appendage (LAA) closure device, pericardial patch, bulking and filling agent, vein valve, heart valve, bone marrow scaffold, meniscus regeneration device, ligament and tendon graft, spinal fusion device, skin substitute, wound healing device, dural substitute, bone graft substitute, wound dressing, ulcer repair device, a hemostat and a surgical mesh wherein the surgical mesh is selected from the group consisting of mesh for face lift, neck lift, eyebrow lift, breast lift and breast reconstruction.

12. A method for preparing the ultrafine fibers claim 1 by electrospinning comprising
  (a) preparing a spinning polymer solution by dissolving the polymer in an organic solvent, wherein the polymer is selected from the group consisting of poly-4-hydroxybutyrate (P4HB) homopolymer; and a blend of P4HB homopolymer with a polymer selected from the group consisting of polymers derived from glycolic acid and lactic acid;
  (b) optionally adding a surfactant to the spinning solution; and
  (c) spinning the solution using an electro-spinner.

13. The method of claim 12 wherein the fibers have a melt temperature of at least 60° C.

14. The organic solvent of claim 13, wherein the solvent is selected from the group consisting of methylene chloride, chloroform, dichloroethane, tetrachloroethane, trichloroethane, dibromomethane, bromoform, tetrahydrofuran, acetone, acetonitrile, dimethylformamide, dimethylsulfoxide, and 1,4-dioxane, alone, or combined into a mixed solvent.

15. The method of claim 13 wherein the spinning solution is ejected through a single nozzle, a plurality of nozzles or co-axial nozzles, wherein the nozzle or nozzles may be stationary or moving.

16. The method of claim 13 wherein the spinning solution is discharged from one or more nozzles of an electro-spinner at a rate between 0.1 to 5.0 cc/min.

17. The method of claim 13 wherein the concentration of the poly-4-hydroxybutyrate homopolymer in the spinning solution is up to 60% by weight.

18. The method of claim 13 wherein the polymer solution is electrospun onto a collector coated or sprayed with an anti-static agent.

19. The method of claim 12 wherein the relative humidity (RH) is in the range of 20-80% RH between the nozzle and the collecting plate of the electro-spinner when the ultrafine fibers are formed.

20. The method of claim 12 wherein the spinning solution is ejected into an applied electrostatic potential between 3 and 100 kV.

21. The method of claim 12 wherein the distance between the nozzle and the collecting plate of the electro-spinner is 5 to 30 cm.

22. The device of claim 9 wherein the device is used for the repair, regeneration or replacement of soft or hard tissue.

23. The device of claim 22 selected from the group consisting of a stent, stent graft, drug delivery device, device for temporary wound or tissue support, device for soft or hard tissue repair or regeneration, repair patch, tissue engineering scaffolds, retention membranes, anti-adhesion membrane, tissue separation membrane, hernia repair device, cardiovascular patch, vascular closure device, sling, rotator cuff repair device, meniscus repair device, guided tissue repair/regeneration device, articular cartilage repair device, osteochondral repair device, bone void filler, nerve guide, tendon repair device, intracardiac septal defect repair device, atrial septal defect repair devices, patent foramen ovale (PFO) closure devices, left atrial appendage (LAA) closure device, pericardial patch, bulking and filling agent, vein valve, heart valve, bone marrow scaffold, meniscus regeneration device, ligament and tendon graft, spinal fusion device, skin substitute, wound healing device, dural substitute, bone graft substitute, wound dressing, ulcer repair device, a hemostat and a surgical mesh wherein the surgical mesh is selected from the group consisting of a mesh for face lift, neck lift, eyebrow lift, breast lift and breast reconstruction.

24. A method of using the device of claim 9 comprising implanting the device into a body.

25. The method of claim 24 wherein the device is selected from the group consisting of a stent, stent graft, drug delivery device, device for temporary wound or tissue support, device for soft or hard tissue repair or regeneration, repair patch, tissue engineering scaffolds, retention membranes anti-adhesion membrane, tissue separation, membrane, hernia repair device, cardiovascular patch, vascular closure device, sling, rotator cuff repair device, meniscus repair device, guided tissue repair/regeneration device, articular cartilage repair device, osteochondral repair device, bone void filler, nerve guide, tendon repair device, intracardiac septal defect repair device, atrial septal defect repair devices, patent foramen ovale (PFO) closure devices, left atrial appendage (LAA) closure device, pericardial patch, bulking and filling agent, vein valve, heart valve, bone marrow scaffold, meniscus regeneration device, ligament and tendon graft, spinal fusion device, skin substitute, wound healing device, dural substitute, bone graft substitute, wound dressing, ulcer repair device, a hemostat and a surgical mesh wherein the surgical mesh is selected from the group consisting of mesh for face lift, neck lift, eyebrow lift, breast lift and breast reconstruction.

26. A medical device comprising a web of non-woven electrospun ultrafine polymeric fibers wherein the fibers have an average diameter of from 10 nm to 10 µm, wherein the ultrafine fibers are derived by preparing a polymer spinning solution by dissolving the polymer in an organic solvent, wherein the polymer is selected from the group consisting of P4HB homopolymer and a blend of P4HB homopolymer with a polymer selected from the group consisting of polymers derived from glycolic acid and lactic acid; and spinning the solution using an electro-spinner.

\* \* \* \* \*

UNITED STATES PATENT AND TRADEMARK OFFICE
CERTIFICATE OF CORRECTION

PATENT NO. : 10,201,640 B2
APPLICATION NO. : 13/800871
DATED : February 12, 2019
INVENTOR(S) : David P. Martin et al.

Page 1 of 1

It is certified that error appears in the above-identified patent and that said Letters Patent is hereby corrected as shown below:

In the Claims

Claim 12, Column 19, Line 40, replace "ultrafine fibers claim 1" with --ultrafine fibers of claim 1--.

Signed and Sealed this
Twenty-fifth Day of February, 2020

Andrei Iancu
*Director of the United States Patent and Trademark Office*